United States Patent
Speronello et al.

(10) Patent No.: US 8,293,283 B2
(45) Date of Patent: *Oct. 23, 2012

(54) METHODS FOR TREATING ORAL CAVITY INFECTIONS WITH CHLORINE DIOXIDE

(75) Inventors: Barry Keven Speronello, Montgomery Township, NJ (US); Frank S. Castellana, Princeton, NJ (US)

(73) Assignee: BASF SE, Ludwigshafen (DE)

( * ) Notice: Subject to any disclaimer, the term of this patent is extended or adjusted under 35 U.S.C. 154(b) by 231 days.

This patent is subject to a terminal disclaimer.

(21) Appl. No.: 12/502,913

(22) Filed: Jul. 14, 2009

(65) Prior Publication Data

US 2010/0015207 A1 Jan. 21, 2010

Related U.S. Application Data

(60) Provisional application No. 61/135,011, filed on Jul. 15, 2008, provisional application No. 61/106,026, filed on Oct. 16, 2008, provisional application No. 61/150,685, filed on Feb. 6, 2009, provisional application No. 61/187,198, filed on Jun. 15, 2009.

(51) Int. Cl.
*A61K 33/20* (2006.01)
*A61K 9/70* (2006.01)
*A61P 31/00* (2006.01)

(52) U.S. Cl. .......... 424/661; 424/53; 424/422; 424/443; 514/772.3

(58) Field of Classification Search ................. 424/49, 424/52, 422, 449
See application file for complete search history.

(56) References Cited

U.S. PATENT DOCUMENTS

| | | |
|---|---|---|
| 2,071,091 A | 2/1937 | Taylor |
| 4,060,600 A | 11/1977 | Vit |
| 4,104,190 A | 8/1978 | Hartshorn |
| 4,330,531 A | 5/1982 | Alliger |
| 4,585,482 A | 4/1986 | Tice |
| 4,683,039 A | 7/1987 | Twardowski |
| 4,689,215 A | 8/1987 | Ratcliff |
| 4,696,811 A | 9/1987 | Ratcliff |
| 4,786,492 A | 11/1988 | Ratcliff |
| 4,788,053 A | 11/1988 | Ratcliff |
| 4,792,442 A | 12/1988 | Ratcliff |
| 4,793,989 A | 12/1988 | Ratcliff |
| 4,808,389 A | 2/1989 | Ratcliff |
| 4,818,519 A | 4/1989 | Ratcliff |
| 4,837,009 A | 6/1989 | Ractliff |
| 4,851,213 A | 7/1989 | Ratcliff |
| 4,855,135 A | 8/1989 | Ratcliff |
| 4,886,657 A | 12/1989 | Ratcliff |
| 4,889,714 A | 12/1989 | Ratcliff |
| 4,925,656 A | 5/1990 | Ratcliff |
| 4,975,285 A | 12/1990 | Ratcliff |
| 5,200,171 A | 4/1993 | Ratcliff |
| 5,227,168 A | 7/1993 | Chvapil |
| 5,281,412 A | 1/1994 | Lukacovic |
| 5,348,734 A | 9/1994 | Ratcliff |
| 5,399,288 A | 3/1995 | Marzouk |
| 5,407,656 A | 4/1995 | Roozdar |
| 5,489,435 A | 2/1996 | Ratcliff |
| 5,597,561 A | 1/1997 | Kross |
| 5,618,550 A | 4/1997 | Ratcliff |
| 5,651,996 A | 7/1997 | Roozdar |
| 5,719,100 A | 2/1998 | Zahradnik |
| 5,820,822 A | 10/1998 | Kross |
| 5,879,691 A | 3/1999 | Sagel |
| 5,944,528 A | 8/1999 | Montgomery |
| 6,007,735 A | 12/1999 | Creed |
| 6,039,934 A | 3/2000 | Alliger |
| 6,046,243 A | 4/2000 | Wellinghoff |
| 6,077,495 A | 6/2000 | Speronello |
| 6,077,502 A | 6/2000 | Witt |
| 6,106,284 A | 8/2000 | Cronin |
| 6,238,643 B1 | 5/2001 | Thangaraj |
| 6,280,775 B1 | 8/2001 | Sasson et al. |
| 6,287,551 B1 | 9/2001 | Ratcliff |
| 6,294,108 B1 | 9/2001 | Speronello |
| 6,294,510 B1 | 9/2001 | Norman |
| 6,312,670 B1 | 11/2001 | Montgomery |
| 6,365,131 B1 | 4/2002 | Doshi et al. |
| 6,379,658 B1 | 4/2002 | Marano |
| 6,425,759 B1 | 7/2002 | Cronin |
| 6,432,322 B1 | 8/2002 | Speronello |
| 6,432,387 B1 | 8/2002 | Laizuka |
| 6,479,037 B1 | 11/2002 | Montgomery |
| 6,500,408 B2 | 12/2002 | Chen |
| 6,551,579 B2 | 4/2003 | Sagel |
| 6,582,682 B2 | 6/2003 | Stier |
| 6,669,931 B2 | 12/2003 | Lynch |
| 6,682,721 B2 | 1/2004 | Kim |
| 6,699,404 B2 | 3/2004 | Speronello |
| 6,759,030 B2 | 7/2004 | Kosti |

(Continued)

FOREIGN PATENT DOCUMENTS

DE 198 54 349 A1 11/1998

(Continued)

OTHER PUBLICATIONS

International Preliminary Report on Patentability dated Jan. 18, 2011 for PCT/US2009/050641 filed Jul. 15, 2009.

(Continued)

*Primary Examiner* — Walter Webb
(74) *Attorney, Agent, or Firm* — Drinker Biddle & Reath LLP

(57) ABSTRACT

Methods, devices, compositions, and systems for the alleviation of oral tissue infections by administration of chlorine dioxide are provided.

20 Claims, No Drawings

U.S. PATENT DOCUMENTS

| | | |
|---|---|---|
| 6,848,905 B2 | 2/2005 | Jacobs |
| 6,896,518 B2 | 5/2005 | Jacobs |
| 6,964,571 B2 | 11/2005 | Andersen |
| 7,004,756 B2 | 2/2006 | Andersen |
| 7,040,897 B2 | 5/2006 | Fischer |
| 7,087,190 B2 | 8/2006 | Hei |
| 7,087,208 B2 | 8/2006 | Sampson |
| 7,182,883 B2 | 2/2007 | Speronello |
| 7,220,367 B2 | 5/2007 | Speronello |
| 7,229,647 B2 | 6/2007 | Lee |
| 7,273,567 B1 | 9/2007 | Wellinghoff |
| 7,514,019 B2 | 4/2009 | Martin |
| 7,534,368 B2 | 5/2009 | Martin |
| 7,875,460 B2 | 1/2011 | Ratcliff |
| 2002/0137728 A1 | 9/2002 | Montgomery |
| 2003/0152528 A1 | 8/2003 | Singh |
| 2003/0235549 A1 | 12/2003 | Singh |
| 2006/0024369 A1 | 2/2006 | Speronello |
| 2006/0045855 A1 | 3/2006 | Sasson |
| 2006/0088498 A1 | 4/2006 | Martin |
| 2006/0099550 A1 | 5/2006 | Faasse |
| 2006/0169949 A1 | 8/2006 | Speronello |
| 2006/0183080 A1 | 8/2006 | Nosov |
| 2006/0223033 A1 | 10/2006 | McLean |
| 2006/0292090 A1 | 12/2006 | Sharma |
| 2007/0172412 A1 | 7/2007 | Hratko |
| 2007/0202095 A1 | 8/2007 | Speronello |
| 2007/0231277 A1 | 10/2007 | Sharma |
| 2007/0239073 A1 | 10/2007 | Schaden et al. |
| 2008/0023668 A1 | 1/2008 | Callerame |
| 2008/0025925 A1 | 1/2008 | Allred |
| 2008/0041400 A1 | 2/2008 | Darnell |
| 2009/0016973 A1 | 1/2009 | Ratcliff |
| 2009/0017548 A1 | 1/2009 | Ratcliff |
| 2010/0009009 A1 | 1/2010 | Young |
| 2010/0074970 A1 | 3/2010 | Ratcliff |
| 2010/0221198 A1 | 9/2010 | Ratcliff |
| 2010/0233101 A1 | 9/2010 | Grootveld |
| 2011/0318282 A1 | 12/2011 | Ratcliff |

FOREIGN PATENT DOCUMENTS

| | | |
|---|---|---|
| DE | 19854349 A1 | 5/2000 |
| EP | 1736135 A1 | 12/2006 |
| JP | 60105610 A | 6/1985 |
| WO | 20060108432 A1 | 10/2006 |
| WO | WO 2007/062347 A2 | 5/2007 |
| WO | WO 2007/079287 A2 | 7/2007 |
| WO | WO 2007/131970 A1 | 11/2007 |
| WO | 20090009163 A1 | 1/2009 |

OTHER PUBLICATIONS

Masschelein, Chlorine Dioxide Chemistry and Environmental Impact of Oxychlorine Compounds, Ann Arbor Science Publishers, Ann Arbor, Michigan, 1979, pp. 138-139.

METHODS FOR TREATING ORAL CAVITY INFECTIONS WITH CHLORINE DIOXIDE

CROSS-REFERENCE TO RELATED APPLICATIONS

This application claims the benefit pursuant to 35 U.S.C. §119(e) of U.S. Provisional Application Nos. 61/135,011, filed on Jul. 15, 2008; 61/106,026, filed Oct. 16, 2008; 61/150,685, filed Feb. 6, 2009; and 61/187,198, filed Jun. 15, 2009, each of which is hereby incorporated by reference in its entirety herein.

BACKGROUND

Infections of the oral cavity, such as of the tissue supporting teeth, are a common problem in mammals, including humans. Oral cavity infections range from caries development, arising from dental plaque bacterial damage to hard tooth tissue, to halitosis, arising from the volatile sulfur compounds (VSCs) produced by bacterial metabolic degradation of organic substances, to gingivitis, the inflammation of the gingiva (i.e., gum tissue) caused by dental plaque, which can progress to periodontis, a family of inflammatory diseases of periodontium. Dental plaque, which is a biofilm, is generally discussed in U.S. Pat. No. 7,497,834. Microorganisms and oral cavity infections are generally discussed in U.S. Publication No. 2009/0016973. Untreated periodontal infections can result in the progressive destruction of alveolar bone, leading to loss of teeth. Furthermore, oral health may be indicative of systemic health (Kim et al., 2006, Odontology 94:10-21). Treatment of oral infection may contribute to ameliorating systemic disease.

Current prophylactic and therapeutic treatments for oral tissue infections include brushing, flossing, topical fluoride, scaling and root planing, antiseptic mouth rinse, such as with a peroxide, antibiotics and, in extreme cases, surgical excision of infected tissue. Chlorine dioxide is known to be a disinfectant, as well as a strong oxidizing agent. The bactericidal, algaecidal, fungicidal, bleaching, and deodorizing properties of chlorine dioxide are also well known. Therapeutic and cosmetic applications for chlorine dioxide are known. For example, U.S. Publication No. 2009/0016973 describes the use of stabilized chlorine dioxide solutions for the prevention of oral disease. U.S. Pat. No. 5,281,412 describes chlorite and chlorine dioxide compositions that provide antiplaque and antigingivitis benefits without staining the teeth.

The traditional method for preparing chlorine dioxide involves reacting sodium chlorite with gaseous chlorine ($Cl_2$ (g)), hypochlorous acid (HOCl), or hydrochloric acid (HCl). The reactions proceed at much greater rates in acidic medium, so substantially all traditional chlorine dioxide generation chemistry results in an acidic product solution having a pH below 3.5. Chlorine dioxide may also be prepared from chlorate anion by either acidification or a combination of acidification and reduction. At ambient conditions, all reactions require strongly acidic conditions; most commonly in the range of 7-9 N. Heating of the reagents to higher temperature and continuous removal of chlorine dioxide from the product solution can reduce the acidity needed to less than 1 N.

A method of preparing chlorine dioxide in situ uses a solution referred to as "stabilized chlorine dioxide." Stabilized chlorine dioxide solutions contain little or no chlorine dioxide, but rather, consist substantially of sodium chlorite at neutral or slightly alkaline pH. Addition of an acid to the sodium chlorite solution activates the sodium chlorite, and chlorine dioxide is generated in situ in the solution. The resulting solution is acidic. Typically, the extent of sodium chlorite conversion to chlorine dioxide is low, and a substantial quantity of sodium chlorite remains in the solution.

The current literature summarized above describes the use of chlorine dioxide compositions and methods that are damaging to biological tissues, including soft tissues such as gums and hard tissues such as tooth enamel and dentin. Methods, compositions, devices and systems for using chlorine dioxide for treatment of oral infection in which biological tissue is not damaged are needed.

SUMMARY

The following embodiments meet and address these needs. The following summary is not an extensive overview. It is intended to neither identify key or critical elements of the various embodiments nor delineate the scope of them.

A method for alleviating an oral cavity tissue infection is provided. The method comprises administering a composition comprising a chlorine dioxide source that includes chlorine dioxide or chlorine dioxide-generating components to the oral cavity, thereby alleviating the infection of the tissue in the oral cavity, wherein the administering step comprises one or more of: i) contacting the tissue with a substantially non-cytotoxic composition comprising the chlorine dioxide source; ii) contacting the tissue with a device comprising the chlorine dioxide source and oxy-chlorine anions, wherein the device delivers a substantially oxy-chlorine anion free chlorine dioxide composition to the tissue; or iii) contacting the tissue with a composition comprising the chlorine dioxide source and oxy-chlorine anions; and a barrier substance that substantially prohibits passage therethrough of the oxy-chlorine anions and permits passage therethrough of a substantially oxy-chlorine anion free chlorine dioxide composition, thereby enabling delivery of the substantially oxy-chlorine anion free chlorine dioxide composition to the tissue. In some embodiments, the oral cavity tissue infection can be selected from the group consisting of halitosis, gingivitis, periodontitis, caries development, and thrush.

In an embodiment, the composition comprises about 1 to about 1000 ppm chlorine dioxide. In another embodiment, the composition comprises about 20 to about 400 ppm chlorine dioxide In some embodiments, the the chlorine dioxide source comprises a particulate precursor of chlorine dioxide as the chlorine dioxide-generating components.

In an embodiment, the composition further comprises an antimicrobial agent. In some embodiments, the antimicrobial agent is selected from the group consisting of: doxycycline, metronidazole, chlorhexidine, minocycline, tetracycline, nystatin, miconazole, and amphotericin.

In another embodiment, the method further comprising administering a second composition comprising an antimicrobial agent to the oral cavity. In some embodiments, the antimicrobial agent is selected from the group consisting of: doxycycline, metronidazole, chlorhexidine, minocycline, tetracycline, nystatin, miconazole, and amphotericin.

In one aspect, the administering step comprises contacting the tissue with a substantially non-cytotoxic composition comprising the chlorine dioxide source. In some embodiments, the substantially non-cytotoxic composition comprises less than about 0.2 milligrams oxy-chlorine anion per gram composition. In some embodiments, the substantially non-cytotoxic composition has a pH from about 4.5 to about 11. In some embodiments, the contacting step comprises a dental strip, a dental film or a dental tray.

In another aspect, the administering step comprises contacting the tissue with a device comprising a chlorine dioxide source and oxy-chlorine anions, wherein the device delivers a substantially oxy-chlorine anion free chlorine dioxide composition to the tissue. In some embodiments, the device comprises: an optional backing layer; a layer comprising the chlorine dioxide source; and a barrier layer interposed between the chlorine dioxide source layer and the tissue, wherein the barrier layer substantially prohibits passage therethrough of the oxy-chlorine anions and permits passage therethrough of the substantially oxy-chlorine anion free chlorine dioxide composition. The barrier film can be a film selected from the group consisting of polyurethane, polypropylene, polytetrafluoroethylene, polyvinylidene difluoride, polyvinylidene dichloride, combination of polydimethylsiloxane and polytetrafluoroethylene, polystyrene, cellulose acetate, polysiloxane, and combinations thereof.

In another embodiment, the device comprises: a backing layer and a matrix affixed to the backing layer, wherein the matrix comprises: a chlorine dioxide source and oxy-chlorine anions; and a barrier substance that substantially prohibits passage therethrough of the oxy-chlorine anions and permits passage therethrough of the substantially oxy-chlorine anion free chlorine dioxide composition. In some embodiments of the device, the barrier substance is selected from the group consisting of polyurethane, polypropylene, polytetrafluoroethylene, polyvinylidene difluoride, polyvinylidene dichloride, combination of polydimethylsiloxane and polytetrafluoroethylene, polystyrene, cellulose acetate, polysiloxane, polyethylene oxide, polyacrylates, mineral oil, paraffin wax, polyisobutylene, polybutene and combinations thereof.

In another embodiment, the administering step comprises contacting the tissue with a composition comprising a chlorine dioxide source, oxy-chlorine anions, and a barrier substance. In some embodiments of the composition, the barrier substance is selected from the group consisting of polyurethane, polypropylene, polytetrafluoroethylene, polyvinylidene difluoride, polyvinylidene dichloride, combination of polydimethylsiloxane and polytetrafluoroethylene, polystyrene, cellulose acetate, polysiloxane, polyethylene oxide, polyacrylates, mineral oil, paraffin wax, polyisobutylene, polybutene, and combinations thereof.

Further provided is a method for alleviating an oral cavity tissue infection, wherein the method comprises administering a composition comprising a chlorine dioxide source to the oral cavity, wherein the administering step comprises contacting the tissue with a substantially non-irritating composition comprising the chlorine dioxide source, thereby alleviating the infection of the tissue in the oral cavity. In some embodiments, the oral cavity tissue infection can be selected from the group consisting of halitosis, gingivitis, periodontitis, caries development, and thrush.

In some embodiments, the substantially non-irritating composition comprises about 1 to about 1000 ppm chlorine dioxide. In other embodiments, the substantially non-irritating composition comprises about 20 to about 400 ppm chlorine dioxide.

In some embodiments, the chlorine dioxide source comprises a particulate precursor of chlorine dioxide as the chlorine dioxide-generating components. In some embodiments, the substantially non-irritating composition comprises less than about 0.2 milligrams oxy-chlorine anion per gram composition. The substantially non-irritating composition can have a pH from about 4.5 to about 11.

In some embodiments, the contacting step comprises a dental strip, a dental film or a dental tray.

In an embodiment, the composition further comprises an antimicrobial agent. In some embodiments, the antimicrobial agent is selected from the group consisting of: doxycycline, metronidazole, chlorhexidine, minocycline, tetracycline, nystatin, miconazole, and amphotericin.

In another embodiment, the method further comprising administering a second composition comprising an antimicrobial agent to the oral cavity. In some embodiments, the antimicrobial agent is selected from the group consisting of: doxycycline, metronidazole, chlorhexidine, minocycline, tetracycline, nystatin, miconazole, and amphotericin.

DETAILED DESCRIPTION

The following description sets forth in detail certain illustrative aspects and implementations of the embodiments. These are indicative, however, of but a few of the various ways in which the principles of the various compositions and devices may be employed. Other objects, advantages, and novel features of the methods will become apparent from the following detailed description.

Chlorine dioxide can be of great utility in a variety of applications in biological systems as a result of its disinfectant, bactericidal, algaecidal, fungicidal, bleaching, and deodorizing properties. However, chlorine dioxide compositions have been determined to be damaging to biological tissues. One aspect arises in part from the inventors' determination that the cytotoxic component in chlorine dioxide compositions is not chlorine dioxide itself. Instead, oxy-chlorine anions present in chlorine dioxide compositions have been determined to be the cytotoxic components. The methods described herein generally pertain to the administration of a composition comprising chlorine dioxide to a tissue in a substantially non-cytotoxic and/or non-irritating manner to alleviate an infection of an oral tissue. The methods described herein are useful in the treatment of any infection of an oral cavity tissue susceptible to topical exposure of a biocidal agent, in particular, chlorine dioxide.

Definitions

Unless defined otherwise, all technical and scientific terms used herein generally have the same meaning as commonly understood by one of ordinary skill in the art. Generally, the nomenclature used herein and the laboratory procedures in cytopathicity analysis, microbial analysis, organic and inorganic chemistry, and dental clinical research are those well known and commonly employed in the art.

As used herein, each of the following terms has the meaning associated with it.

The articles "a" and "an" are used herein to refer to one or to more than one (i.e., to at least one) of the grammatical object of the article. By way of example, "an element" means one element or more than one element.

It is understood that any and all whole or partial integers between any ranges set forth herein are included herein.

The term "about" will be understood by persons of ordinary skill in the art and will vary to some extent on the context in which it is used. Generally, "about" encompasses a range of values that are approximately plus/minus 10% of a reference value. For instance, "about 25%" encompasses values from approximately 22.5% to approximately 27.5%.

As used herein, an "oral cavity infection" refers to a disease or disorder of a tissue in an oral cavity caused by a pathogenic infection. The pathogen may be bacterial, viral or fungal. A oral disease encompasses conditions wherein if the disease is not ameliorated then the animal's oral health continues to deteriorate. In contrast, an oral disorder is a state of oral health in which the animal is able to maintain homeostasis, but in which the animal's state of health is less favorable than it would be in the absence of the disorder. Left untreated, a disorder does not necessarily cause a further decrease in the animal's state of oral health. The term encompasses periodontal disease, halitosis, thrush and dental caries development.

As used herein, a "periodontal disease" is an infection of the tissues that support a subject's teeth, caused by a pathogenic infection. Periodontal disease includes gingivitis and periodontitis.

As used herein, a "biofilm" refers to a biological aggregate that forms a layer on a surface, the aggregate comprising a community of microorganisms embedded in an extracellular matrix of polymers. Typically, a biofilm comprises a diverse community of microorganisms, including bacteria (aerobic and anaerobic), algae, protozoa and fungi. Monospecies biofilms also exist.

As used herein, "dental plaque" refers to a biofilm that forms on the surface of teeth.

As used herein, a disease or disorder is "alleviated" if the severity of a symptom of the disease or disorder, the frequency with which such a symptom is experienced by a patient, or both, are reduced.

A "therapeutic" treatment is a treatment administered to a subject who exhibits signs of pathology for the purpose of diminishing or eliminating those signs.

A "prophylactic" treatment is a treatment administered to a subject who does not exhibit signs of a disease or exhibits only early signs of the disease for the purpose of decreasing the risk of developing pathology associated with the disease.

As used herein, "biocidal" refers to the property of inactivating or killing pathogens, such as bacteria, algae, viruses, and fungi (e.g., anti-bacterial, anti-algal, antiviral and antifungal).

The term "chlorine dioxide-generating components" refers to at least an oxy-chlorine anion source and an activator of chlorine dioxide generation. In some embodiments, the activator is an acid source. In these embodiments, the components optionally further includes a free halogen source. The free halogen source may be a cationic halogen source, such as chlorine. In other embodiments, the activator is an energy-activatable catalyst. In yet other embodiments, the activator is a dry or anhydrous polar material.

The term "polar material" as used herein, refers to a material which has, as a result of its molecular structure, an electrical dipole moment on a molecular scale. Most commonly, polar materials are organic materials which comprise chemical elements with differing electronegativities. Elements that can induce polarity in organic materials include oxygen, nitrogen, sulfur, halogens, and metals. Polarity may be present in a material to different degrees. A material may be considered more polar if its molecular dipole moment is large, and less polar if its molecular dipole moment is small. For example, ethanol, which supports the electronegativity of the hydroxyl over a short, 2-carbon chain may be considered relatively more polar compared to hexanol ($C_6H_{13}OH$) which supports the same degree of electronegativity over a 6-carbon chain. The dielectric constant of a material is a convenient measure of polarity of a material. A suitable polar material has a dielectric constant, measured at about 18-25° C., of greater than 2.5. The term "polar material" excludes water and aqueous materials. A polar material may be a solid, a liquid, or a gas.

The term "dry," as used herein, means a material which contains very little free water, adsorbed water, or water of crystallization.

The term "anhydrous," as used herein, means a material that does not contain water, such as free water, adsorbed water or water of crystallization. An anhydrous material is also dry, as defined above. However, a dry material is not necessarily anhydrous, as defined herein.

An "efficacious amount" of an agent is intended to mean any amount of the agent that will result in a desired biological effect. That result can be reduction and/or alleviation of the signs, symptoms, or causes of a disease, or any other desired alteration of a biological system. For an oral tissue infection, reduction in the: extent of infection, duration of infection and/or frequency of infection can be used to gauge an efficacious amount. An appropriate therapeutic amount in any individual case may be determined by one of ordinary skill in the art using routine experimentation.

By "cytotoxic" is meant the property of causing lethal or sublethal damage to mammalian cell structure or function. A composition is deemed "substantially non-cytotoxic" or "not substantially cytotoxic" if the composition meets the United States Pharmacopeia (USP) biological reactivity limits of the Agar Diffusion Test of USP <87> "Biological Reactivity, in vitro," (approved protocol current in 2007) when the active pharmaceutical ingredient (API) is present in an efficacious amount.

As used herein, "irritating" refers to the property of causing a local inflammatory response, such as reddening, swelling, itching, burning, or blistering, by immediate, prolonged, or repeated contact. For example, inflammation of the gingival tissue in a mammal is an indication of irritation to that tissue. A composition is deemed "substantially non-irritating" or "not substantially irritating," if the composition is judged to be slightly or not irritating using any standard method for assessing dermal or mucosal irritation. Non-limiting examples of methods useful for assessing dermal irritation include the use of in vitro tests using tissue-engineered dermal tissue, such as EpiDerm™ (MatTek Corp., Ashland, Mass.), which is a human skin tissue model (see, for instance, Chatterjee et al., 2006, *Toxicol Letters* 167: 85-94) or ex vivo dermis samples. Non-limiting examples of methods useful for mucosal irritation include: HET-CAM (hen's egg test-chorioallantoic membrane); slug mucosal irritation test; and in vitro tests using tissue-engineered oral mucosa or vaginal-ectocervical tissues. Other useful method of irritation measurement include in vivo methods, such as dermal irritation of rat or rabbit skin (e.g., the Draize skin test (OECD, 2002, Test Guidelines 404, Acute Dermal Irritation/Corrosion) and EPA Health Effects Testing Guidelines; OPPTS 870.2500 Acute Dermal Irritation). The skilled artisan is familiar with art-recognized methods of assessing dermal or mucosal irritation.

By "oxy-chlorine anion" is meant chlorite ($ClO_2^-$) and/or chlorate ($ClO_3^-$) anions.

By "substantially oxy-chlorine anion free chlorine dioxide composition" is meant a composition that contains an efficacious amount of chlorine dioxide and a non-cytotoxic and/or non-irritating concentration of oxychlorine anion, all as defined hereinabove. The composition may contain other components or may consist essentially of oxy-chlorine anion free chlorine dioxide. The composition may be a gas or vapor comprising or consisting essentially of chlorine dioxide, but may be any type of fluid, including a solution or a thickened fluid. The composition may be an aqueous fluid or a non-aqueous fluid.

By "stable" is meant that the components used to form chlorine dioxide, i.e., the chlorine dioxide forming ingredients, are not immediately reactive with each other to form chlorine dioxide. It will be understood that the components may be combined in any fashion, such as sequentially and/or simultaneously, so long as the combination is stable until such time that ClO₂ is to be generated.

By "non-reactive" is meant that a component or ingredient as used is not immediately reactive to an unacceptable degree with other components or ingredients present to form chlorine dioxide or mitigate the ability of any component or ingredient to perform its function in the formulation at the necessary time. As the skilled artisan will recognize, the acceptable timeframe for non-reactivity will depend upon a number of factors, including how the formulation is to be formulated and stored, how long it is to be stored, and how the formulation is to be used. Accordingly, "not immediately reactive" will range from one or more minutes, to one or more hours, to one or more weeks.

The phrase "thickened fluid composition" encompasses compositions which can flow under applied shear stress and which have an apparent viscosity when flowing that is greater than the viscosity of the corresponding aqueous chlorine dioxide solution of the same concentration. This encompasses the full spectrum of thickened fluid compositions, including: fluids that exhibit Newtonian flow (where the ratio of shear rate to shear stress is constant and independent of shear stress), thixotropic fluids (which require a minimum yield stress to be overcome prior to flow, and which also exhibit shear thinning with sustained shear), pseudoplastic and plastic fluids (which require a minimum yield stress to be overcome prior to flow), dilatant fluid compositions (which increase in apparent viscosity with increasing shear rate) and other materials which can flow under applied yield stress.

A "thickener component" refers to a component that has the property of thickening a solution or mixture to which it is added. A "thickener component" is used to make a "thickened fluid composition" as described herein and above.

By "apparent viscosity" is meant the ratio of shear stress to shear rate at any set of shear conditions which result in flow. Apparent viscosity is independent of shear stress for Newtonian fluids and varies with shear rate for non-Newtonian fluid compositions.

The term "hydrophobic" or "water-insoluble," as used with respect to organic polymers refers to an organic polymer, which has a water solubility of less than about one gram per 100 grams of water at 25° C.

By "acid source" is meant a material, usually a particulate solid material, which is itself acidic or produces an acidic environment when in contact with liquid water or solid oxychlorine anion.

The term "particulate" is defined to mean all solid materials. By way of a non-limiting example, particulates may be interspersed with each other to contact one another in some way. These solid materials include particles comprising big particles, small particles or a combination of both big and small particles.

By "source of free halogen" and "free halogen source" is meant a compound or mixtures of compounds which release halogen upon reaction with water.

By "free halogen" is meant halogen as released by a free halogen source.

By "particulate precursor of chlorine dioxide" is meant a mixture of chlorine-dioxide-forming components that are particulate. Granules of ASEPTROL (BASF, Florham Park, N.J.) are an exemplary particulate precursor of chlorine dioxide.

By "solid body" is meant a solid shape, preferably a porous solid shape, or a tablet comprising a mixture of granular particulate ingredients wherein the size of the particulate ingredients is substantially smaller than the size of the solid body; by "substantially smaller" is meant at least 50% of the particles have a particle size at least one order of magnitude, and preferably at least two orders of magnitude, smaller than the size of solid body.

By "oxidizing agent" is meant any material that attracts electrons, thereby oxidizing another atom or molecule and thereby undergoing reduction. Exemplary oxidizing agents include chlorine dioxide and peroxides, such as hydrogen peroxide.

A "matrix," as used herein, is a material that functions as a protective carrier of chlorine dioxide-generating components. A matrix is typically a continuous solid or fluid phase in the materials that can participate in a reaction to form chlorine dioxide are suspended or otherwise contained. The matrix can provide physical shape for the material. If sufficiently hydrophobic, a matrix may protect the materials within from contact with moisture. If sufficiently rigid, a matrix may be formed into a structural member. If sufficiently fluid, a matrix may function as a vehicle to transport the material within the matrix. If sufficiently adhesive, the matrix can provide a means to adhere the material to an inclined or vertical, or horizontal downward surface. A fluid matrix may be a liquid such that it flows immediately upon application of a shear stress, or it may require that a yield stress threshold be exceeded to cause flow. In some embodiments, the matrix is either a fluid, or capable of becoming fluid (e.g., upon heating) such that other components may be combined with and into the matrix (e.g., to initiate reaction to form chlorine dioxide). In other embodiments, the matrix is a continuous solid; chlorine dioxide generation can be initiated by, for instance, penetration of water or water vapor, or by light activation of an energy-activatable catalyst.

By "film" is meant a layer of a material having two dimensions substantially larger than the third dimension. A film may be a liquid or a solid material. For some materials, a liquid film can be converted info a solid film by curing, for instance, by evaporation, heating, drying and/or cross-linking.

Unless otherwise indicated or evident from context, preferences indicated above and herein apply to the entirety of the embodiments discussed herein.

Description

Chlorine dioxide has well-documented potent biocidal activity. Disadvantageously, chlorine dioxide-containing compositions of the prior art can be cytotoxic and irritating to soft and damaging to hard tissues. The cytotoxicity of chlorine dioxide-containing compositions results predominantly from the presence of oxy-chlorine anions, and not from the presence of chlorine, which can be a product of chlorine dioxide decomposition. By substantially preventing or inhibiting oxy-chlorine anions present in a chlorine-dioxide containing composition from contacting cells and tissues, including hard tooth tissues such as enamel and dentin and soft oral tissues, such as oral mucosa and gums, that are targeted for treatment, tissue damage can be measurably reduced or minimized. Soft oral tissues include buccal mucosa, other oral cavity mucosa (e.g., soft palate mucosa, floor of mouth mucosa and mucosa under the tongue) and the tongue. Accordingly, methods are provided herein for the alleviation of an oral cavity tissue infection by administering a chlorine dioxide composition in a non-cytotoxic and/or non-irritating manner.

The method described can be used for alleviating any infection of oral cavity tissue. Infections of oral cavity tissue include, but are not limited to, halitosis, gingivitis, periodontitis, caries formation, and thrush. Oral tissue may be intact or may have one or more incisions, lacerations or other tissue-penetrating opening. The methods may be practiced prophylactically or therapeutically.

Bacteria in the oral cavity can produce volatile sulfur compounds (VSCs) which underlie oral malodor or halitosis. VSCs include hydrogen sulfide, methylmercaptan and dimehtylmercaptan. The bacteria that contribute to this problem include: *Fusobacterium nucleatum, Treponema denticola, Tannerella forsythia* (formerly *Bacteroides forsythus*), *Prevotella intermedia, Porphyromonas gingivalis, Porphyromonas endodontalis*, and *Eubacterium* species.

Oral cavity infections that are related to dental plaque include caries development, gingivitis and periodontitis. While hundreds of bacteria have been detected in dental plaque, the most common bacteria that contribute to gingivitis and periodontitis are: *Actinobacillus actinomycetemcomitans, Campylobacter rectus, Eikenella corrodens* and seven anaerobic species, *Porphyromonas gingivalis, Bacteroides forsythus, Treponema denticola, Prevotella intermedia, Fusobacterium nucleatum, Eubacterium*, and spirochetes. *P. gingivalis*, a gram-negative anaerobe, is believed to be largely responsible for adult periodontitis. Various herpes viruses have been found to contribute to destructive periodontal disease. The bacteria that largely underlie caries formation are *Streptococcus mutan, Lactobacillus acidophilus, Actinomyces viscosus*, and *Nocardia* spp.

Oral thrush is the most common oral fungal infection. The causative agents of oral thrush are *Candida albicans* and *Candida dubliniensis*. *C. dubliniensis* is typically found in immunocompromised patien, such as AIDS patients, organ transplant patients and patients undergoing chemotherapy.

The method can comprise a single administration of the composition comprising chlorine dioxide or chlorine dioxide-generating components. In other embodiments, the method comprises one or more iterations of the contacting step. In yet other embodiments, the composition comprises a second therapeutic agent in addition to the chlorine dioxide. In an embodiment, the second therapeutic agent is an antimicrobial agent, such as an antibiotic or antifungal agent.

The method can further comprise alternating treatment steps wherein one step comprises administration of a composition comprising a chlorine dioxide source and a second step comprises administration of a composition comprising a second, non-chlorine-dioxide therapeutic agent. These steps may take place in any order and in multiple iterations. Consecutive steps may comprise the same composition or different compositions.

The method can comprise two or more sequential steps of treatment with the composition comprising a chlorine dioxide source, followed by at least one step of treatment with the other therapeutic agent. The number and/and duration of treatments with the composition comprising a chlorine dioxide source may be the same or different as the number and/or duration of treatments with the second therapeutic composition. The composition comprising a chlorine dioxide source may be identical in the plural steps or may be different, such as a different concentration of chlorine dioxide. Similarly, the second therapeutic agent composition may be identical in the plural steps or may be different. Likewise, the duration of treatment steps may be the same or different for the composition comprising a chlorine dioxide source and for the second therapeutic agent composition.

I. Non-Cytotoxic and/or Non-Irritating Compositions

In one aspect, the method comprises administering a substantially non-cytotoxic and/or non-irritating composition comprising chlorine dioxide. In an embodiment, the composition consists essentially of chlorine dioxide as the active pharmaceutical ingredient (API). In other embodiments, the composition comprises chlorine dioxide and at least one other API, such as an antibiotic. The composition optionally comprises one or more other components. Such components include, but are not limited to, sweetners, flavorants, coloring agents and fragrances. Other optional components include: antimicrobial agents such as antibacterial agents and antifungal agents, enzymes, malodor controlling agents, cleaning agents, such as phosphates, antigingivitis agents, antiplaque agents, antitartar agents, anticaries agents, such as a source of fluoride ion, antiperiodontitis agents, nutrients, antioxidants, and the like. Exemplary antimicrobial agents include but are not limited to: doxycycline, metronidazole, chlorhexidine, minocycline and tetracycline. Exemplary antifungal agents include, but are not limited to, miconazoel, nystatin and amphotericin.

It is preferred that all optional components are relatively resistant to oxidation by chlorine dioxide, since oxidation of composition components by chlorine dioxide will reduce the available chlorine dioxide for oxidation for its intended function. "Relatively resistant" means that in the time scale of preparing and using the chlorine dioxide-containing composition in an application, the function of the optional component is not unacceptably diminished, and the composition retains an acceptable level of efficacy/potency with respect to the chlorine dioxide and remains substantially non-cytotoxic. In some embodiments, the composition preferably also remains substantially non-irritating.

For compositions comprising an oxidizing agent consisting of chlorine dioxide, cytotoxicity results predominantly from the presence of oxy-chlorine anions. Accordingly, a composition comprising chlorine dioxide that comprises zero milligram (mg) oxy-chlorine anion per gram composition to no more than about 0.25 mg oxy-chlorine anion per gram composition, preferably zero to 0.24, 0.23, 0.22, 0.21, or 0.20 mg oxy-chlorine anion per gram composition, more preferably zero to 0.19, 0.18, 0.17, 0.16, 0.15, 0.14, 0.13, 0.12, 0.11, or 0.10 mg oxy-chlorine anion per gram composition and more preferably still from zero to 0.09, 0.08, 0.07, 0.06, 0.05 or 0.04 mg oxy-chlorine anion per gram composition, absent other constituents that contribute to cytotoxicity, is substantially non-cytotoxic.

Soft tissue irritation can result from highly reactive oxygen species and/or extremes of pH, both acidic and basic. To minimize soft tissue irritation by the chlorine dioxide containing composition, the substantially non-cytotoxic composition has a pH of at least 3.5. Preferably, the composition has a pH of at least 5, and more preferably still, greater than about 6. In certain embodiments, the pH ranges from about 4.5 to about 11, more preferably from about 5 to about 9, and more preferably still, greater than about 6 and less than about 8. In one embodiment, the pH is about 6.5 to about 7.5. The concentration of oxy-chlorine anions is not believed to be a primary contributor to soft tissue irritation.

Methods of preparing non-cytotoxic and/or non-irritating compositions comprising chlorine dioxide are described in commonly-assigned U.S. provisional application No. 61/135,011, filed Jul. 15, 2008, entitled "Tooth Whitening Compositions and Methods," 61/106,026, filed Oct. 16, 2008, entitled "Tooth Whitening Compositions and Methods" and 61/150,685, filed Feb. 6, 2009, entitled "Non-Cytotoxic Chlorine Dioxide Fluids," and each of which is incorporated herein by reference in its entirety.

In an embodiment, a substantially non-cytotoxic composition comprising chlorine dioxide can be prepared using a substantially pure chlorine dioxide solution having a neutral pH. In some embodiments, the substantially pure chlorine dioxide solution has a pH from about 5 to about 9, and more preferably, from about 6.5 to about 7.5.

Substantially pure chlorine dioxide may be prepared by any known method, then bubbling a gas (e.g., air) through that solution (sparging) and into a second container of deionized water, to prepare the product solution of substantially pure chlorine dioxide. Only $ClO_2$ and possibly some water vapor is transferred from the source solution to the product solution. All the salt ingredients and acid remain behind in the source solution. Thus, there are no oxy-chlorine anions in the substantially pure product solution. One method of preparing chlorine dioxide comprises combining an aqueous solution of sodium chlorite with a mineral acid to reduce the solution pH to below about 3.5 and allowing the solution to react for a sufficient time, e.g., about 30 minutes, to generate chlorine dioxide. The resulting solution is then sparged as described above to prepare the product solution of substantially pure chlorine dioxide.

While the substantially pure chlorine dioxide may undergo a degree of decomposition, the rate is relatively slow. By keeping the solution capped and protected from ultraviolet exposure, the decomposition rate can be slowed to a rate of about 5% to about 25% reduction in chlorine dioxide in 7 days. Substantially pure chlorine dioxide may also be prepared using a pervaporation technique, such as that disclosed in U.S. Pat. No. 4,683,039. In addition, a metal chlorite and an acid source can be reacted in solution to yield high conversion to chlorine dioxide and produce a greater than 2000 ppm chlorine dioxide solution. The concentrated solution can then be buffered to a neutral pH. Similarly, a chlorine dioxide solution can be prepared using the composition described in U.S. Pat. No. 5,399,288, which yields a high concentration chlorine dioxide solution at acidic pH. The concentrated solution can then be buffered to achieve a substantially neutral pH to prepare a substantially pure chlorine dioxide solution.

Another source of a substantially pure chlorine dioxide solution is chlorine dioxide is prepared using an ASEPTROL (BASF Corp., Florham Park, N.J.) material, which are described in commonly-assigned U.S. Pat. Nos. 6,432,322 and 6,699,404. These patents disclose substantially anhydrous solid bodies comprising particulate components for preparing highly-converted solutions of chlorine dioxide when added to water. The particulate components in the solid bodies comprise a metal chlorite such as sodium chlorite, an acid source such as sodium bisulfate and optionally a source of free halogen such as the sodium salt of dichloroisocyanuric acid or a hydrate thereof (collectively referred to herein as "NaDCCA"). Chlorine dioxide is generated when an ASEPTROL material is contacted with water or an aqueous medium. ASEPTROL material can be made to have an extremely high conversion rate in an aqueous solution, as described in U.S. Pat. Nos. 6,432,322 and 6,699,404, resulting in high concentrations of chlorine dioxide and low concentrations of oxy-chlorine anion. Thus, ASEPTROL materials provide a way to efficiently generate chlorine dioxide at substantially neutral pH, thus avoiding problems existing with earlier, acidic chlorine dioxide-based products.

In some embodiments, the composition further comprises a thickener component which renders the composition a thickened aqueous fluid. To prepare a thickened aqueous composition comprising chlorine dioxide that is substantially non-cytotoxic and, in some embodiments, non-irritating, the substantially pure chlorine dioxide solution can be combined with a thickener component and an aqueous medium.

The aqueous thickened fluid composition used in practicing the method may comprise any thickener component in an aqueous medium, wherein the thickened fluid composition is non-cytotoxic and, in some embodiments, non-irritating to soft tissues. In addition, the thickener is preferably not adversely affected by the chlorine dioxide on the time scale of composition preparation and use in treatment. Many thickener agents are known in the art, including, but not limited to carbomers (e.g., CARBOPOL thickeners, Lubrizol Corp., Wickliffe, Ohio), carboxymethylcellulose (CMC), ethylcellulose, hydroxyethylcellulose, hydroxypropyl cellulose, natural smectite clays (e.g., VEEGEM, R.T. Vanderbilt Co., Norwalk, Conn.), synthetic clays (e.g., LAPONITE (Southern Clay Products, Gonzales, Tex.), methylcellulose, superabsorbent polymers such as polyacrylates (e.g., LUQUASORB 1010, BASF, Florham Park, N.J.), poloxamers (PLURONIC, BASF, Florham Park, N.J.), polyvinyl alcohol, sodium alginate, tragacanth, and xanthan gum. Such thickening agents may be categorized into four groups: natural hydrocolloids (also referred to as "gum"), semisynthetic hydrocolloids, synthetic hydrocolloids, and clay. Some examples of natural hydrocolloids include acacia, tragacanth, alginic acid, carrageenan, locust bean gum, guar gum, and gelatin. Non-limiting examples of semisynthetic hydrocolloids include methylcellulose and sodium carboxymethylcellulose. Some examples of synthetic hydrocolloids (also referred to as "polymers" including polymers, cross-linked polymers, and copolymers) include polyacrylates, superabsorbent polymers, high molecular weight polyethylene glycols and polypropylene glycols, polyethylene oxides and CARBOPOL. Non-limiting examples of clay (including swelling clay) include LAPONITE, attapulgite, bentonite and VEEGUM. Preferably the thickener component is a semisynthetic hydrocolloid. More preferably, the thickener component is a carboxymethylcellulose (CMC).

In preparing a non-cytotoxic composition, one or more components of a composition may be combined prior to the time of preparation of a composition. Alternatively, all components of a composition may be prepared at the time of use. For either non-cytotoxic solutions or non-cytotoxic thickened compositions, optional other components suitable for the intended use of the non-cytotoxic chlorine dioxide solution, as described elsewhere herein, may be included. Chlorine dioxide in solution will decompose over time. To avoid problems arising from such decomposition, including loss of efficacy and generation of chlorite anions, the substantially pure chlorine dioxide solution is preferably prepared immediately before its dilution or its combination with a thickener component and an aqueous medium.

In addition, a thickened composition comprising chlorine dioxide is preferably prepared immediately before its use in a method of alleviating an oral tissue infection. "Immediately before" as used herein refers to a period no greater than that which would result in diminished efficacy or evidence of cytotoxicity. Generally, "immediately before" is less than about 14 days, and preferably no greater than about 24 hours and more preferably no greater than about 2 hours. Preferably, the substantially pure chlorine dioxide solution is prepared within about 8 hours of the preparation of the composition. Precautions are also taken to avoid exposing the chlorine dioxide solution or the prepared composition to strong ultraviolet light or elevated temperature (e.g., temperature greater than ambient temperature, about 25° C.).

A substantially non-cytotoxic thickened composition comprising chlorine dioxide may also be prepared using a particulate precursor of $ClO_2$ and an aqueous thickened fluid composition. Chlorine-dioxide-forming components include metal chlorites, metal chlorates, an acid source and an optional halogen source. The particulate precursor may comprise one of these or any combination of these. Preferably the particulate precursor is an ASEPTROL product, more preferably it is ASEPTROL S-Tab2. ASEPTROL S-Tab2 has the following chemical composition by weight (%): $NaClO_2$ (7%); $NaHSO_4$ (12%); NaDCC (1%); NaCl (40%); $MgCl_2$ (40%). Example 4 of U.S. Pat. No. 6,432,322 describes an exemplary manufacture process of S-Tab2. Granules can be produced, either by comminuting pressed S-Tab2 tablets, or by dry roller compaction of the non-pressed powder of the S-Tab2 components, followed by breakup of the resultant compacted ribbon or briquettes, and then screening to obtain the desired size granule. Upon exposure to water or an aqueous thickened fluid, chlorine dioxide is generated from the ASEPTROL granules. In one embodiment, a substantially non-cytotoxic composition comprising chlorine dioxide is prepared by combining −40 mesh granules with an aqueous thickened fluid. In one embodiment, the thickener component of the thickened fluid is carboxymethylcellulose. The skilled artisan will recognize that chlorine dioxide production in the thickened fluid composition prepared using a particulate precursor of $ClO_2$, while rapid, is not instantaneous. Thus, sufficient time for the generation of chlorine dioxide, and corresponding consumption of chlorite anion, is necessary to obtain a substantially non-cytotoxic thickened fluid composition. The skilled artisan can readily determine what time is sufficient, in view of the teachings in this disclosure and the knowledge of the art.

Preferably, the aqueous thickened fluid is prepared sufficiently in advance of combining with the ASEPTROL granules to enable the complete hydration of the thickener component. In one embodiment, the thickened fluid composition is formed by adding high viscosity NaCMC powder to distilled water. The NaCMC is allowed to hydrate for at least 8 hours, and then the mixture is stirred to homogenize it. A substantially non-cytotoxic composition is then prepared by mixing the sized ASEPTROL granules with the NaCMC thickened fluid. Contact with the aqueous medium in the hydrated NaCMC mixture activates the ASEPTROL granules and chlorine dioxide is generated.

In another embodiment, the substantially non-cytotoxic thickened fluid composition may also be formed at the site of intended use. For instance, a body fluid, such as saliva, mucus of mucosal tissue or humid vapor such as exhaled air, may serve as the aqueous medium to activate particulate precursors of chlorine dioxide, such as ASEPTROL granules. In one embodiment, the mixture may be particulates in the form of a powder and mixed in a layer of thickener component thereby forming a thickened matrix. The matrix may be applied directly to an oral tissue, wherein exposure to moisture present in the tissue activates production of chlorine dioxide to form a substantially non-cytotoxic composition. Alternatively, the matrix may be moistened immediately prior to use and then applied to an oral tissue. In another embodiment, a mixture of ASEPTROL granules and a thickener component is formed into a shape, for instance by addition of a malleable wax, and the shape is then applied to teeth. Saliva activates the granules, forming chlorine dioxide and the thickener component hydrates, thereby forming the thickened fluid composition in situ. In another embodiment, a mixture of ASEPTROL granules and a thickener component is placed on a dental strip, a dental film or in a dental tray. A dental strip refers to a substantially planar object made of a plastic backbone that is sufficiently flexible to affix to teeth. A dental film refers to a substantially planar object made of a pliable, conformable material that can be substantially fitted to the surface of teeth. Optionally, the dental strip is dissolvable in an aqueous medium, such as saliva. The strip, film or tray is positioned on teeth, and saliva serves as the aqueous medium as described above to produce the substantially non-cytotoxic thickened fluid composition in situ. Alternatively, the mixture on the strip or tray is contacted with water or aqueous medium prior to positioning on the teeth. In another embodiment, the substantially non-cytotoxic and/or non-irritating composition, thickened or non-thickened, is in the form of an oral rinse.

II. Devices and Compositions for Non-Cytotoxic Administration

In another aspect, the method is practiced with a device or composition that delivers a substantially oxy-chlorine anion free chlorine dioxide composition to the oral tissue. Such devices, compositions, systems and methods for administration of a composition comprising chlorine dioxide and oxy-chlorine anions in a way that the chlorine dioxide reaches the target tissue in an efficacious amount, but the oxy-chlorine anions are substantially inhibited from irritating target tissue or peripheral tissue not targeted for treatment, are described in commonly-assigned U.S. provisional application No. 61/187,198, filed Jun. 15, 2009, entitled "Methods, Systems and Devices for Administration of Chlorine Dioxide." Generally, the method comprises providing a chlorine dioxide source that includes either chlorine dioxide itself or chlorine dioxide-generating components, and further includes the oxy-chlorine anions that cause cytotoxicity to tissues; and further providing an oxy-chlorine anion barrier that substantially prohibits passage therethrough of the oxy-chlorine anions and permits passage therethrough of chlorine dioxide. In some embodiments, the oxy-chlorine anion barrier can also substantially inhibit the passage therethrough of protons. The chlorine dioxide source is applied to the tissue with the oxy-chlorine anion barrier interposed between the chlorine dioxide source and the tissue, thus preventing or substantially minimizing the oxy-chlorine anion from reaching the tissue, thereby enabling delivery of a substantially oxy-chlorine anion free chlorine dioxide composition to the tissue.

The chlorine dioxide source may comprise any chlorine dioxide-containing composition or ingredients capable of forming chlorine dioxide in situ. The ingredients present in the chlorine dioxide source are preferably compatible with the oxy-chlorine anion barrier during the practice of the method, as well as any pre-use period during which the ingredients are in contact with the barrier. By "compatible" is meant the ingredients do not adversely affect to an unacceptable degree the concentration of chlorine dioxide in the chlorine dioxide source, the inhibition of passage of oxy-chlorine anions, or the permitted passage of chlorine dioxide by the barrier.

The barrier may be in the form of a layer between the chlorine dioxide source and the infected oral tissue. In one aspect, the oxy-chlorine barrier, without the chlorine dioxide source, is applied to the tissue first. The chlorine dioxide source is then applied to the barrier layer. In other embodiments, the chlorine dioxide source is applied to the barrier first, and the combination is then applied to the tissue, wherein the barrier layer contacts the tissue. In embodiments where the chlorine dioxide source comprises chlorine dioxide-generating components, the generation of chlorine dioxide may be activated before, during, and/or after application of the barrier (with or without the chlorine dioxide source) to the oral cavity tissue.

In another embodiment, the infected tissue may be contacted with a chlorine dioxide source containing a substantially non-cytotoxic and substantially non-irritating amount of oxy-chlorine anions while a second chlorine dioxide source may be located on the side of a barrier opposite the oral tissue such that additional chlorine dioxide from the second source may pass through the barrier to contact the oral tissue but passage through the barrier of oxy-chlorine anions in the second source is inhibited.

In another embodiment, the chlorine dioxide source may be dispersed in a matrix comprising one or more barrier substances, such that the oxy-chlorine anions are sequestered away from the tissue, while the chlorine dioxide passes through the barrier substance, if necessary, and the matrix to contact the oral tissue. In this embodiment, the matrix is applied to the tissue directly or to an optional intervening tissue-contacting layer. In one aspect, the matrix itself is the barrier substance. Exemplary matrix materials that may also function as the barrier include waxes such as paraffin wax, polyethylene, petrolatum, polysiloxanes, polyvinyl alcohol, ethylene-vinyl acetate (EVA), polyurethanes, mixtures thereof and the like. In another aspect, the chlorine dioxide source is coated or encapsulated by the barrier substance. Exemplary barrier substances include polyurethane, polypropylene, polytetrafluoroethylene, polyvinylidene difluoride, polyvinylidene dichloride, combination of polydimethylsiloxane and polytetrafluoroethylene, polystyrene, cellulose acetate, polysiloxane, polyethylene oxide, polyacrylates, mineral oil, paraffin wax, polyisobutylene, polybutene and combinations thereof. Exemplary barrier substances also comprise compounds that bind to oxy-chlorine anions with high affinity and that impede or stop anion migration or diffusion such that a substantially oxy-chlorine anion free chlorine dioxide composition is delivered to a tissue. The compound may form an insoluble precipitate with the oxy-chlorine anion, thereby impeding or stopping diffusion. Alternatively, the compound is immobilized on a substance or material, thereby impeding diffusion or migration. The compound may be cationic, such as ammonium, pyridinium, imidazolium, phosphonium and sulfonium and other positively charged compounds that may be part of the matrix. Optionally, the compound can be immobilized on an oxy-chlorine anion barrier material, to the matrix or on the optional backing layer.

Various materials and membranes can be used as an oxy-chlorine anion barrier. The barrier can be in any form, and is typically either a fluid or a solid.

In other embodiments, the oxy-chlorine anion barrier is a fluid, such a petrolatum. In this embodiment, the fluid may be applied to the tissue first, or to an intervening tissue-contacting layer, to form the barrier as a layer and then chlorine dioxide source subsequently applied to the fluid barrier layer. The chlorine dioxide source may be applied as a particulate or may be encompassed in a material to form a film.

In some embodiments, the oxy-chlorine anion barrier is a nonporous membrane. The membrane can be any thickness and can be a single layer or plural layers, provided the membrane remains permeable to chlorine dioxide and substantially non-permeable to oxy-chlorine anions. An exemplary nonporous material is a polyurethane membrane. In some embodiments, the polyurethane membrane is from about 30 to about 100 microns, such as from about 38 to about 76 microns thick. Exemplary polyurethane membranes commercially available include CoTran™ 9701 (3M™ Drug Delivery Systems, St. Paul, Minn.) and ELASTOLLAN (BASF Corp., Wyandotte, Mich.). ELASTOLLAN products are polyether-based thermoplastic polyurethane. A specific example of ELASTOLLAN is ELASTOLLAN 1185A10.

In some embodiments, the oxy-chlorine anion barrier is a microporous membrane permeable to chlorine dioxide and substantially non-permeable to oxy-chlorine anions. The microporous membrane can be any thickness and can be a single layer or plural layers, provided the membrane remains permeable to chlorine dioxide and substantially non-permeable to oxy-chlorine anions. In one example, the microporous membrane can comprise thermo-mechanically expanded polytetrafluoroethylene (e.g., Goretex®) or polyvinylidenedifluoride (PVDF). See, for instance, U.S. Pat. No. 4,683,039. The procedure for formation of an expanded polytetrafluoroethylene is described in U.S. Pat. No. 3,953,566. An exemplary polytetrafluoroethylene (PTFE) membrane, interpenetrating polymer network (IPN) of polydimethylsiloxane and PTFE, is described in U.S. Pat. Nos. 4,832,009, 4,945,125, and 5,980,923. A commercially-available product of this type, Silon-IPN (Bio Med Sciences Inc., Allentown, Pa.), is a single layer and is available in thicknesses between 10 to 750 microns. In one embodiment, the microporous membrane is an IPN of silicone and PTFE having a thickness of about 16 microns. In another example, the membrane is microporous polypropylene film. An exemplary microporous polypropylene film is the material commercially-available from CHEMPLEX Industries (Palm City, Fla.), which is a single layer membrane about 25 microns thick, having a porosity of 55% and a pore size of about 0.21 microns×0.05 microns. The microporous membrane material may be provided as a composite with supporting materials to provide the structural strength required for use. In some embodiments, the membrane is hydrophobic, wherein the hydrophobic nature of the membrane prevents both an aqueous reaction medium and an aqueous recipient medium from passing through the membrane, while allowing molecular diffusion of chlorine dioxide. Features to consider for the materials used for such a barrier include: hydrophobicity of the microporous material, pore size, thickness, and chemical stability towards the attack of chlorine dioxide, chlorine, chlorite, chlorate, chloride, acid, and base.

Various other materials and membranes can be used to form the barrier. For example, the barrier can comprise a microperforated polyolefin membrane; a polystyrene film that is substantially permeable to chlorine dioxide and substantially impermeable to ionic components of the composition; a pervaporation membrane formed from a polymeric material having a relatively open polymeric structure; a cellulose acetate film composite; a polysiloxane or polyurethane material; or a wax. Of course, for contact with soft tissues, the microporous barrier should be substantially non-irritating and substantially non-cytotoxic, particularly in the time scale of typical use of the device and composition.

The pore sizes in the barrier may vary widely, depending on the desired flow rate of the chlorine dioxide through the barrier. The pores should not be so small as to prevent chlorine dioxide gas flow therethrough but also should not be so large that liquid flow is permitted. In one embodiment, the pore size is about 0.21 microns×0.05 microns. The quantity and size of the pores of the barrier may vary widely, depending upon the temperature of the application, the hydrophobicity of the barrier material, the thickness of the barrier material, and also depending upon the desired flow rate of chlorine dioxide through the barrier. Fewer and smaller pores are needed for a given chlorine dioxide flow rate at higher temperature relative to lower temperature, as the vapor pressure of chlorine dioxide from the chlorine dioxide source is higher at the higher temperature. More and larger pores may be used with a highly hydrophobic barrier material, such as PTFE, compared to a less hydrophobic material, such as polyurethane, since the tendency for an aqueous chlorine dioxide source to flow through pores of a highly hydrophobic barrier is lower than it is through the pores of a less hydrophobic barrier. Considerations of barrier strength also dictate the porosity chosen.

Generally, the barrier porosity varies from about 1 to about 98%, from about 25 to about 98%, or from about 50% to about 98%.

Also provided are systems, compositions, and devices useful for practicing the method.

In one aspect, a system is provided for delivering a substantially oxy-chlorine anion free chlorine dioxide to a tissue. A typical system comprises a chlorine dioxide source that includes chlorine dioxide or chlorine dioxide-generating components, and oxy-chlorine anions as a first system component; and an oxy-chlorine anion barrier as a second system component, the barrier to be interposed between the chlorine dioxide source and the tissue, wherein the barrier substantially prohibits passage of the oxy-chlorine anions and permits passage of the substantially oxy-chlorine anion free chlorine dioxide composition, thereby enabling delivery of the substantially oxy-chlorine anion free chlorine dioxide to the tissue.

Compositions and devices are also provided to implement the methods and systems described above. Thus, one aspect features a composition for delivering a substantially oxy-chlorine anion free chlorine dioxide composition to a tissue. The composition comprises a matrix that includes a chlorine dioxide source comprising chlorine dioxide or chlorine dioxide-generating components, as well as oxy-chlorine anions, and at least one barrier substance that substantially prohibits passage of the oxy-chlorine anions but permits passage of the chlorine dioxide, thereby enabling delivery of the substantially oxy-chlorine anion free chlorine dioxide to the tissue. In one embodiment, the matrix can be a aqueous matrix, or a hydrophobic or anhydrous matrix such as petrolatum. In some embodiments, the matrix itself is the barrier substance. For instance, the matrix can be nonpolar or weakly polar for inhibiting diffusion of oxy-chlorine anions while permitting diffusion of chlorine dioxide.

The bulk of the matrix can be the barrier substance, or the matrix can comprise a sufficient amount of the barrier substance to carry out the selective delivery of the chlorine dioxide to the oral tissue. For instance, the matrix can comprise a polymeric material in which reactants or precursors for the formation of chlorine dioxide are embedded or dispersed, wherein the polymeric material is permeable to chlorine dioxide but substantially impermeable to oxy-chlorine anions. See, e.g., U.S. Pat. No. 7,273,56, which describes a composition comprising reactants or precursors and an energy-activatable catalyst embedded in polyethylene, which are activated to produce chlorine dioxide by exposure to light waves, and more particularly, by exposure to ultraviolet radiation.

In some embodiments, the matrix is an adhesive matrix, such as an adhesive polymer matrix. Polymers useful in such adhesive matrices are substantially permeable to chlorine dioxide and are preferably relatively resistant to oxidation by chlorine dioxide so as to limit possible degradation of the polymer and possible consequential change in adhesion. Adhesive polymers are known in the art. See, e.g., U.S. Pat. No. 7,384,650.

The composition can be applied to the tissue, e.g., by spreading it on or otherwise applying it to the tissue, or by incorporating it into a delivery device, such as described below.

Various devices are envisioned for delivering a composition comprising chlorine dioxide and oxy-chlorine anions to target oral tissue such that an efficacious amount of chlorine dioxide contacts the target tissue, while the oxy-chlorine anions are substantially inhibited or prevented from contacting the tissue. The substantial inhibition reduces, minimizes or precludes damage or irritation to, the target tissue and any surrounding or peripheral oral hard or soft tissues.

The devices are typically directionally oriented to comprise a layer distal to the tissue to be contacted and a layer proximal to the oral tissue to be contacted. The distal layer is also referred to herein as a backing layer. The devices may further comprise a release liner affixed to the tissue-contacting layer, to be removed prior to applying the device to the tissue. In one embodiment, the device comprises a layer comprising the chlorine dioxide source and a barrier layer. In another embodiment, the device comprises (1) a backing layer, (2) a layer comprising the chlorine dioxide source, and (3) a barrier layer. The barrier layer may be adapted to contact the oral tissue, or another tissue-contacting layer may be present between the barrier layer and the tissue. The barrier layer or the additional tissue-contacting layer can be adhesive. The optional additional tissue-contacting layer is also substantially permeable to chlorine dioxide. In some embodiments, the barrier layer can be made from a thermo-mechanically expanded polytetrafluoroethylene film. In some embodiments, the chlorine dioxide source is a particulate precursor of chlorine dioxide, such as granules of ASEPTROL.

Generally, the backing layer can be made of any suitable material that is substantially impermeable to chlorine dioxide and other components of the chlorine dioxide source. The backing layer may serve as a protective cover for the matrix layer and may also provide a support function. Exemplary materials for the backing layer include films of high and low-density polyethylene, polyvinylidene dichloride (PVDC), polyvinylidene difluoride (PVDF), polypropylene, polyurethane, metal foils and the like.

The optional tissue-contactinging layer can be any material that is substantially permeable to chlorine dioxide. The optional tissue-contactinging layer may be an absorbent material. Non-limiting examples for this layer include cotton or other natural fiber or synthetic fiber fabrics or meshes, foams and mats.

In another embodiment, the device comprises a backing layer and a matrix as described above, in which is dispersed the chlorine dioxide source and which comprises at least one barrier substance. The matrix may be adapted for contacting the tissue, or an additional tissue-contacting layer may be present. Either the matrix or the additional tissue-contacting layer can be adhesive. Typically, the matrix is prepared and then coated onto the backing layer.

Also contemplated is a device for continuously and/or intermittently providing a chlorine dioxide solution containing oxy-chlorine anions to a specific tissue. The device is a modification of the irrigation device described in commonly-assigned U.S. Application No. 61/149,784. The modification is the addition of an oxy-chlorine anion barrier. Specifically, the device contemplated herein comprises a chamber comprising an oxy-chlorine anion barrier, wherein the device has an inlet port for supplying a chlorine dioxide solution into the chamber and an outlet port for removing chlorine dioxide solution and an opening covered by the oxy-chlorine anion barrier. The chamber is designed to form a tight substantially leak-proof seal with the tissue surrounding an infected area, wherein the opening is proximal to the infected area. The oxy-chlorine anion barrier is interposed between the infected area and the chamber opening. The chlorine dioxide solution containing oxy-chlorine anions is introduced into the chamber, and chlorine dioxide passes through the oxy-chlorine anion barrier covering the opening and thereby contacting the infected area, while the passage of oxy-chlorine anions through the barrier is limited to substantially non-cytotoxic and/or substantially non-irritating levels. This device, like the others described herein, enables the use of highly concentrated chlorine dioxide solutions (e.g., much greater than about 700 ppm) while minimizing or eliminating the cytotoxicity of oxy-chlorine anion typically found in such solutions.

Any method in the art for preparing chlorine dioxide may be used as the chlorine dioxide source to make chlorine dioxide. For instance, there are a number of methods of preparing chlorine dioxide by reacting chlorite ions in water to produce chlorine dioxide gas dissolved in water. The traditional method for preparing chlorine dioxide involves reacting sodium chlorite with gaseous chlorine ($Cl_2(g)$), hypochlorous acid (HOCl), or hydrochloric acid (HCl). However, because the kinetics of chlorine dioxide formation are high order in chlorite anion concentration, chlorine dioxide generation is generally done at high concentration (>1000 ppm), the resulting chlorine dioxide containing solution typically must be diluted for the use concentration of a given application. Chlorine dioxide may also be prepared from chlorate anion by either acidification or a combination of acidification and reduction. Chlorine dioxide can also be produced by reacting chlorite ions with organic acid anhydrides.

Chlorine dioxide-generating compositions, which are comprised of materials that will generate chlorine dioxide gas upon contact with water vapor, are known in the art. See, e.g., commonly-assigned U.S. Pat. Nos. 6,077,495; 6,294,108; and 7,220,367. U.S. Pat. No. 6,046,243 discloses composites of chlorite salt dissolved in a hydrophilic material and an acid releasing agent in a hydrophobic material. The composite generates chlorine dioxide upon exposure to moisture. Commonly-assigned U.S. Pat. Publication No. 2006/0024369 discloses a chlorine dioxide-generating composite comprising a chlorine dioxide-generating material integrated into an organic matrix. Chlorine dioxide is generated when the composite is exposed to water vapor or electromagnetic energy. Chlorine dioxide generation from a dry or anhydrous chlorine dioxide-generating composition by activation with a dry polar material is disclosed in commonly-assigned co-pending Application No. 61/153,847. U.S. Pat. No. 7,273,567 describes a method of preparing chlorine dioxide from a composition comprising a source of chlorite anions and an energy-activatable catalyst. Exposure of the composition to the appropriate electromagnetic energy activates the catalyst which in turn catalyzes production of chlorine dioxide gas.

Chlorine dioxide solutions can also be produced from solid mixtures, including powders, granules, and solid compacts such as tablets and briquettes, which are comprised of components that will generate chlorine dioxide gas when contacted with liquid water. See, for instance, commonly-assigned U.S. Pat. Nos. 6,432,322; 6,699,404; and 7,182,883; and U.S. Pat. Publication Nos. 2006/0169949 and 2007/0172412. In preferred embodiments, chlorine dioxide is generated from a composition comprising a particulate precursor of chlorine dioxide. Thus, the chlorine dioxide source comprises or consists essentially of a particulate precursor of chlorine dioxide. The particulate precursor employed can be an ASEPTROL product, such ASEPTROL S-Tab2 and ASEPTROL S-Tab10. ASEPTROL S-Tab2 has the following chemical composition by weight (%): $NaClO_2$ (7%); $NaHSO_4$ (12%); sodium dichloroisocyanurate dihydrate (NaDCC) (1%); NaCl (40%); $MgCl_2$ (40%). Example 4 of U.S. Pat. No. 6,432,322 describes an exemplary manufacture process of S-Tab2 tablets. ASEPTROL S-Tab10 has the following chemical composition by weight (%): $NaClO_2$ (26%); $NaHSO_4$ (26%); NaDCC (7%); NaCl (20%); $MgCl_2$ (21%). Example 5 of U.S. Pat. No. 6,432,322 describes an exemplary manufacture process of S-Tab10 tablets.

As described elsewhere herein, activation of chlorine dioxide generation can be prior to administration by contact of the chlorine dioxide-generating components with the appropriate agent (e.g., aqueous medium, electromagnetic energy, etc). Alternatively, chlorine dioxide generation initiated in situ, by contact with an aqueous medium, such as saliva or exhaled breath.

III. Chlorine Dioxide-generating Components

Chlorine dioxide-generating components refers to at least an oxy-chlorine anion source and an activator of chlorine dioxide generation. In some embodiments, the activator is an acid source. In these embodiments, the components optionally further includes a free halogen source. The free halogen source may be a cationic halogen source, such as chlorine. In other embodiments, the activator is an energy-activatable catalyst. In yet other embodiments, the activator is a dry or anhydrous polar material.

Oxy-chlorine anion sources generally include chlorites and chlorates. The oxy-chlorine anion source may be an alkali metal chlorite salt, an alkaline earth metal chlorite salt, an alkali metal chlorate salt, an alkaline earth metal chlorate salt and combinations of such salts. Metal chlorites are preferred. Preferred metal chlorites are alkali metal chlorites, such as sodium chlorite and potassium chlorite. Alkaline earth metal chlorites can also be employed. Examples of alkaline earth metal chlorites include barium chlorite, calcium chlorite, and magnesium chlorite. An exemplary metal chlorite is sodium chlorite.

For chlorine dioxide generation activated by an acid source, the acid source may include inorganic acid salts, salts comprising the anions of strong acids and cations of weak bases, acids that can liberate protons into solution when contacted with water, organic acids, inorganic acids, and mixtures thereof. In some aspects, the acid source is a particulate solid material which does not react substantially with the metal chlorite during dry storage, however, does react with the metal chlorite to form chlorine dioxide when in the presence of an aqueous medium. The acid source may be water soluble, substantially insoluble in water, or intermediate between the two. Exemplary acid sources are those which produce a pH of below about 7, more preferably below about 5.

Exemplary substantially water-soluble, acid-source-forming components include, but are not limited to, water-soluble solid acids such as boric acid, citric acid, tartaric acid, water soluble organic acid anhydrides such as maleic anhydride, and water soluble acid salts such as calcium chloride, magnesium chloride, magnesium nitrate, lithium chloride, magnesium sulfate, aluminum sulfate, sodium acid sulfate ($NaHSO_4$), sodium dihydrogen phosphate ($NaH_2PO_4$), potassium acid sulfate ($KHSO_4$), potassium dihydrogen phosphate ($KH_2PO_4$), and mixtures thereof. Exemplary acid-source-forming component is sodium acid sulfate (sodium bisulfate). Additional water-soluble, acid-source-forming components will be known to those skilled in the art.

Chlorine dioxide-generating components optionally comprise a source of free halogen. In one embodiment, the free halogen source is a free chlorine source, and the free halogen is free chlorine. Suitable examples of free halogen source used in the anhydrous compositions include dichloroisocyanuric acid and salts thereof such as NaDCCA, trichlorocyanuric acid, salts of hypochlorous acid such as sodium, potassium and calcium hypochlorite, bromochlorodimethylhydantoin, dibromodimethylhydantoin and the like. An exemplary source of free halogen is NaDCCA.

For chlorine dioxide generation activated by an energy-activatable catalyst, the energy-activatable catalyst is selected from the group consisting of a metal oxide, a metal sulfide, and a metal phosphide. Exemplary energy-activatable catalysts include metal oxides selected from the group consisting of titanium dioxide ($TiO_2$); zinc oxide (ZnO); tungsten trioxide ($WO_3$); ruthenium dioxide ($RuO_2$); iridium dioxide ($IrO_2$); tin dioxide ($SnO_2$); strontium titanate ($SrTiO_3$); barium titanate ($BaTiO_3$); tantalum oxide ($Ta_2O_5$); calcium titanate ($CaTiO_3$); iron (III) oxide ($Fe_2O_3$); molybdenum trioxide ($MoO_3$); niobium pentoxide ($NbO_5$); indium trioxide ($In_2O_3$); cadmium oxide (CdO); hafnium oxide ($HfO_2$); zirconium oxide ($ZrO_2$); manganese dioxide ($MnO_2$); copper oxide ($Cu_2O$); vanadium pentoxide ($V_2O_5$); chromium trioxide ($CrO_3$); yttrium trioxide ($YO_3$); silver oxide ($Ag_2O$), $Ti_xZr_{1-x}O_2$ wherein x is between 0 and 1, and combinations thereof. The energy-activatable catalyst can be selected from the group consisting of titanium oxide, zinc oxide, calcium titanate, zirconium oxide and combinations thereof.

Chlorine dioxide-generating components optionally may be present in a matrix. Such matrices may be organic matrices, such as those described in commonly-assigned U.S. Pat. Publication No. 2006/0024369. In these matrices, chlorine dioxide is generated when the composite is exposed to water vapor or electromagnetic energy. The matrix may be a hydrous gel or an anhydrous gel. Hydrophobic matrices may also be employed. Hydrophobic matrix materials include water-impervious solid components such as hydrophobic waxes, water-impervious fluids such as hydrophobic oils, and mixtures of hydrophobic solids and hydrophobic fluids. In embodiments using a hydrophobic matrix, activation of chlorine dioxide may be a dry or anhydrous polar material, as described in co-pending U.S. Application No. 61/153,847.

IV. Treatment Regimens

The dosage of the composition varies within wide limits and may be adjusted to the individual requirements in each particular case. The dosage depends on the condition treated, the general state of health of the recipient, the number and frequency of administrations and other variables known to those of skill in the art. Accordingly, the amount of chlorine dioxide to be delivered to an oral tissue (i.e., an efficacious amount) will relate to the result intended from the application of chlorine dioxide to the tissue. The skilled artisan can readily determine the appropriate amount or amount range of chlorine dioxide to be efficacious for a given use. Generally, useful amounts comprise, for example, from about 1 to about 2000 ppm chlorine dioxide, at least about 1 to about 1000 ppm or at least about 20 to about 400 ppm. In some embodiments, the chlorine dioxide is present in the composition in at least about 5 ppm, at least about 20 ppm, or at least about 30 ppm. Typically, the amount of chlorine dioxide can range to about 1000 ppm, up to about 700 ppm, up to about 500 ppm and up to about 200 ppm. In one embodiment, the composition comprises about 30 to about 100 ppm chlorine dioxide. In some embodiments, a useful dose range can be from about 2.5 mg chlorine dioxide per area of contact (in square meters) to about 500 mg/m$^2$ chlorine dioxide. Doses of at least about 10 mg/m$^2$, at least about 15 mg/m$^2$ and at least about 20 mg/m$^2$ can also be useful.

The composition may be administered to a subject as frequently as several times daily, or it may be administered less frequently, such as once, once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, etc.

The chlorine dioxide that comes into contact with the tissue is substantially oxy-chlorine anion free. In one embodiment, the substantially oxy-chlorine anion free chlorine dioxide that contacts the tissue comprises zero milligram (mg) oxy-chlorine anion per gram to no more than about 0.25 mg oxy-chlorine anion per gram, or from zero to 0.24, 0.23, 0.22, 0.21, or 0.20 mg oxy-chlorine anion per gram composition, or from zero to 0.19, 0.18, 0.17, 0.16, 0.15, 0.14, 0.13, 0.12, 0.11, or 0.10 mg oxy-chlorine anion per gram composition, or from zero to 0.09, 0.08, 0.07, 0.06, 0.05 or 0.04 mg oxy-chlorine anion per gram composition, absent other constituents that contribute to cytotoxicity, and is therefore substantially non-cytotoxic. In some embodiments, the substantially oxy-chlorine anion free chlorine dioxide comprises less than about 400 milligrams per square meter of contact area, less than about 375 mg/m$^2$, less than about 350 mg/m$^2$, than about 325 mg/m$^2$, or than about 300 mg/m$^2$ oxy-chlorine anions. In some embodiments, the substantially oxy-chlorine anion free chlorine dioxide comprises from zero to less than about 200 mg/m$^2$ oxy-chlorine anions. In other embodiments, the substantially oxy-chlorine anion free chlorine dioxide comprises from zero to less than about 100 mg/m$^2$ oxy-chlorine anions.

Oxy-chlorine anions can be measured in chlorine dioxide solutions or compositions using any method known to those skilled in the art, including ion chromatography following the general procedures of EPA test method 300 (Pfaff, 1993, "Method 300.0 Determination of Inorganic Anions by Ion Chromatography," Rev. 2.1, US Environmental Protection Agency) or a titration method based on an amperometric method (Amperometric Method II in Eaton et al, ed., "Standard Methods for the Examination of Water and Wastewater" 19$^{th}$ edition, American Public Health Association, Washington D.C., 1995). Alternatively, oxy-chlorine anions may be measured by a titration technique equivalent to the amperometric method, but which uses the oxidation of iodide to iodine and subsequent titration with sodium thiosulfate to a starch endpoint in place of the amperometric titration; this method is referred to herein as "pH 7 buffered titration." A chlorite analytical standard can be prepared from technical grade solid sodium chlorite, which is generally assumed to comprise about 80% by weight of pure sodium chlorite.

The disclosures of each and every patent, patent application, and publication cited herein are hereby incorporated herein by reference in their entirety.

While methods, devices, compositions, and systems described have been disclosed with reference to specific embodiments, it is apparent that other embodiments and variations may be devised by others skilled in the art without departing from the true spirit and scope of the methods, devices, compositions, and systems. The appended claims are intended to be construed to include all such embodiments and equivalent variations.

What is claimed is:

1. A method for alleviating an infection of a tissue in an oral cavity, the method comprising administering a composition comprising a chlorine dioxide source and oxy-chlorine anions to the oral cavity, wherein the composition comprises choline dioxide, thereby alleviating the infection of the tissue in the oral cavity, wherein the administering step comprises one or more of:
 i) contacting the tissue with a composition comprising the chlorine dioxide source and oxy-chlorine anions, wherein the composition comprises at least about 5 ppm chlorine dioxide and no more than about 0.25 milligrams oxy-chlorine anion per gram composition and is a substantially non-cytotoxic composition;

ii) contacting the tissue with a device comprising the chlorine dioxide source and oxy-chlorine anions, wherein the device delivers a substantially oxy-chlorine anion free chlorine dioxide composition comprising no more than about 0.25 milligrams oxy-chlorine anion per gram composition to the tissue; or iii) contacting the tissue with a composition comprising the chlorine dioxide source and oxy-chlorine anions; and a barrier substance that substantially prohibits passage therethrough of the oxy-chlorine anions and permits passage therethrough of a substantially oxy-chlorine anion free chlorine dioxide composition comprising no more than about 0.25 milligrams oxy-chlorine anion per gram composition, thereby delivering the substantially oxy-chlorine anion free chlorine dioxide composition to the tissue.

2. The method of claim 1, wherein the composition administered to the tissue comprises about 20 to about 1000 ppm chlorine dioxide.

3. The method of claim 1, wherein the composition administered to the tissue comprises about 20 to about 400 ppm chlorine dioxide.

4. The method of claim 1, wherein the chlorine dioxide source comprises a particulate precursor of chlorine dioxide that generates the chlorine dioxide in the composition.

5. The method of claim 1, wherein the oral cavity tissue infection is selected from the group consisting of halitosis, gingivitis, periodontitis, caries development, and thrush.

6. The method of claim 1, wherein the composition administered to the tissue further comprises an antimicrobial agent.

7. The method of claim 6, wherein the antimicrobial agent is selected from the group consisting of: doxycycline, metronidazole, chlorhexidine, minocycline, tetracycline, nystatin, miconazole, and amphotericin.

8. The method of claim 1, further comprising administering a second composition comprising an antimicrobial agent to the oral cavity.

9. The method of claim 1, wherein the administering step comprises i) contacting the tissue with the composition comprising the chlorine dioxide source and oxy-chlorine anions, wherein the composition comprises at least about 5 ppm chlorine dioxide and no more than about 0.25 milligrams oxy-chlorine anion per gram composition and is a substantially non-cytotoxic composition.

10. The method of claim 9, wherein the composition comprises less than about 0.2 milligrams oxy-chlorine anion per gram composition.

11. The method of claim 9, wherein the composition has a pH from about 4.5 to about 11.

12. The method of claim 9, wherein the contacting step comprises a dental strip, a dental film or a dental tray.

13. The method of claim 1, wherein the administering step comprises ii) contacting the tissue with the device comprising the chlorine dioxide source and oxy-chlorine anions, wherein the device delivers the substantially oxy-chlorine anion free chlorine dioxide composition comprising no more than about 0.25 milligrams oxy-chlorine anion per gram composition to the tissue.

14. The method of claim 13, wherein the device comprises:
an optional backing layer;
a layer comprising the chlorine dioxide source; and
a barrier layer interposed between the chlorine dioxide source layer and the tissue, wherein the barrier layer substantially prohibits passage therethrough of the oxy-chlorine anions and permits passage therethrough of the substantially oxy-chlorine anion free chlorine dioxide composition comprising no more than about 0.25 milligrams oxy-chlorine anion per gram composition.

15. The method of claim 14, wherein the barrier layer is a film selected from the group consisting of polyurethane, polypropylene, polytetrafluoroethylene, polyvinylidene difluoride, polyvinylidene dichloride, combination of polydimethylsiloxane and polytetrafluoroethylene, polystyrene, cellulose acetate, polysiloxane, and combinations thereof.

16. The method of claim 13, wherein the device comprises;
a backing layer and a matrix affixed to the backing layer, wherein the matrix comprises:
the chlorine dioxide source and oxy-chlorine anions; and
a barrier substance that substantially prohibits passage therethrough of the oxy-chlorine anions and permits passage therethrough of the substantially oxy-chlorine anion free chlorine dioxide composition comprising no more than about 0.25 milligrams oxy-chlorine anion per gram composition.

17. The method of claim 16, wherein the barrier substance is selected from the group consisting of polyurethane, polypropylene, polytetrafluoroethylene, polyvinylidene difluoride, polyvinylidene dichloride, combination of polydimethylsiloxane and polytetrafluoroethylene, polystyrene, cellulose acetate, polysiloxane, polyethylene oxide, polyacrylates, mineral oil, paraffin wax, polyisobutylene, polybutene and combinations thereof.

18. The method of claim 1, wherein the administering step comprises iii) contacting the tissue with the composition comprising the chlorine dioxide source, oxy-chlorine anions, and the barrier substance.

19. The method of claim 18, wherein the barrier substance is selected from the group consisting of polyurethane, polypropylene, polytetrafluoroethylene, polyvinylidene difluoride, polyvinylidene dichloride, combination of polydimethylsiloxane and polytetrafluoroethylene, polystyrene, cellulose acetate, polysiloxane, polyethylene oxide, polyacrylates, mineral oil, paraffin wax, polyisobutylene, polybutene, and combinations thereof.

20. The method of claim 9, wherein the composition comprising the chlorine dioxide source and oxy-chlorine anions further comprises a thickener.

* * * * *